United States Patent [19]

Johnson et al.

[11] 4,126,709

[45] Nov. 21, 1978

[54] METHOD FOR EXTRACTING CAROTENOID PIGMENTS FROM CITRUS OILS

[75] Inventors: Joseph D. Johnson, Longwood; Hector E. Viale, Ocala; Donald M. Wait, Winter Park, all of Fla.

[73] Assignee: Citrus Central, Inc., Orlando, Fla.

[21] Appl. No.: 769,872

[22] Filed: Feb. 18, 1977

[51] Int. Cl.$^2$ .............................................. A23L 1/27
[52] U.S. Cl. .................................. 426/540; 426/489; 426/492; 260/340.6; 260/236.6
[58] Field of Search ............... 426/250, 540, 615, 616, 426/478, 482, 489, 492, 494; 260/340.6, 236.6

[56] References Cited

U.S. PATENT DOCUMENTS

| 3,523,138 | 8/1970 | Grant | 426/540 |
| 3,725,083 | 4/1973 | Barron et al. | 426/250 |
| 3,906,112 | 9/1975 | Anderson | 426/540 |

OTHER PUBLICATIONS

Burdick, E. M., Extraction and Utilization of Carotenes and Xanthophylls, Economic Botany, 1956, pp. 267–279.

*Primary Examiner*—Jeanette M. Hunter
*Attorney, Agent, or Firm*—Duckworth, Hobby, Allen & Pettis

[57] ABSTRACT

Deriving carotenoid coloring agents from citrus by extracting the natural peel oil from the flavedo of the fruit, treating the oil to remove the undesirable sterols, coumarins and other undesirable waxes therein, and thereafter deterpenating the de-waxed oil by successively folding the oil to a concentration of at least 15-fold in order to remove the major portion of the limonene therein. The de-waxed and deterpenated oil is then distilled under vacuum in a molecular still at a pressure between about 10 microns to 1.0 millimeters of mercury, and at a temperature of between 90° to 120° C to remove the balance of the unwanted constituents and to provide the desired concentrated carotenoids as an output thereof.

19 Claims, 1 Drawing Figure

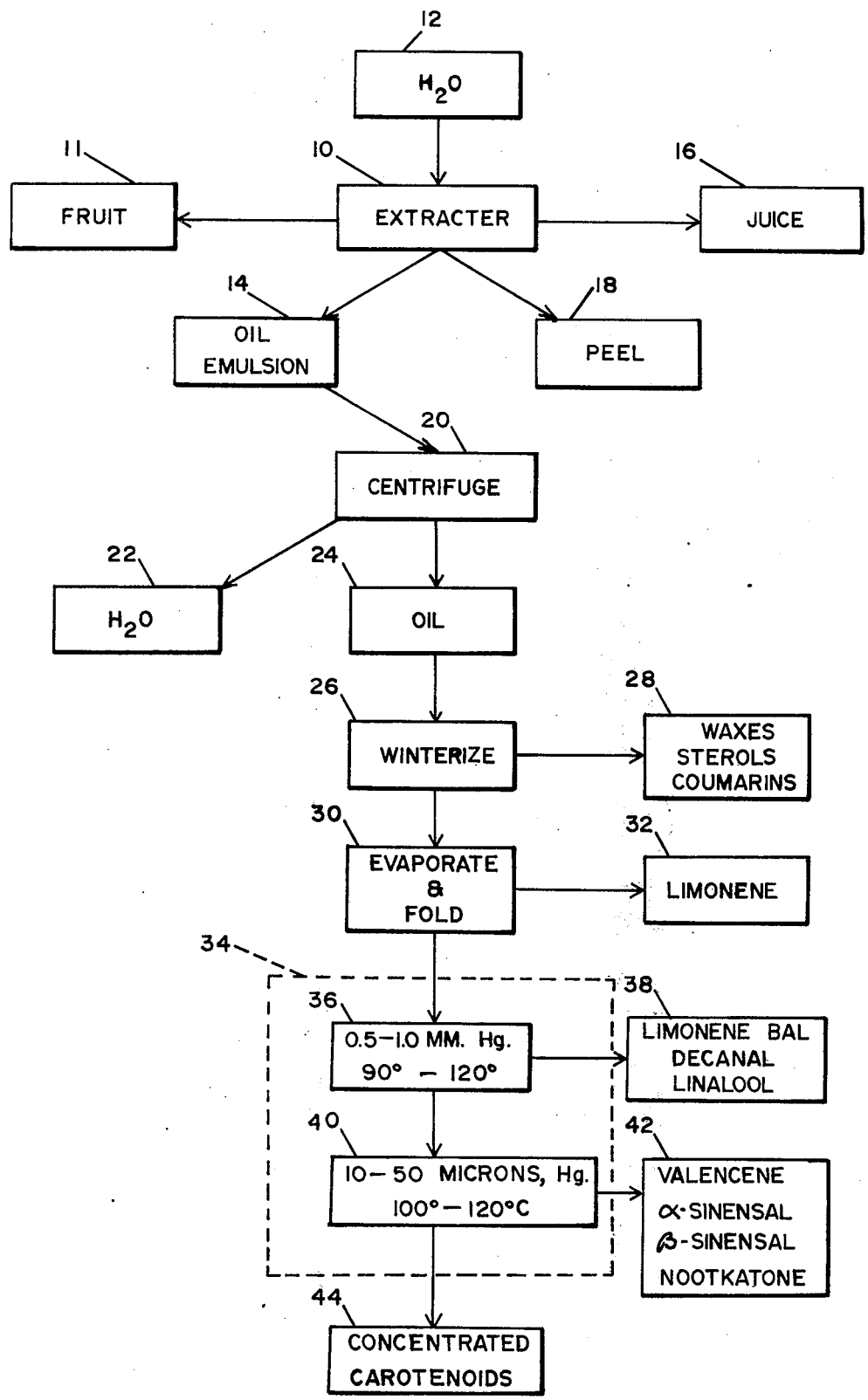

METHOD FOR EXTRACTING CAROTENOID PIGMENTS FROM CITRUS OILS

BACKGROUND OF THE INVENTION

1. Field of the Invention

The present invention relates to methods for removing coloring agents (carotenoids), from citrus fruits, and in particular relates to such methods which avoid the introduction of foreign substances, in order to maintain the natural purity of the resulting product.

2. Description of the Prior Art

Citrus fruits, such as oranges, include an outer, colored skin (referred to as the "flavedo") and an inner, white skin (the "albedo"). The flavedo is made up of a multitude of tiny cells, each containing a complex liquid generally referred to as "peel oil." This peel oil includes, among many others, compounds which establish the color and flavor of the peel and the fruit. The coloring agents in the peel, which are referred to generically as carotenoids, are themselves a complex mixture of organic compounds.

The carotenoids of orange peels potentially have many important commerical uses. For example, juices prepared from fruit in the early part of the growing season often have poor coloring. It is possible to add carotenoids extracted from the peel to "bolster" the color of early season products. Further, such coloring agents have many commerical uses in the coloring of other food products. However, agricultural regulations prohibit the addition of foreign substances, such as organic solvents, to citrus juices and other edibles. As is described further below, the prior art teaches the use of such organic solvents as a means for deriving carotenoids from the flavedo.

These prior art teachings suggest numerous techniques for extracting the carotenoid coloring agents found in the flavedo. In the *Proceedings of the Florida State Horticultural Society*, volume 81, pages 264–268 (1968), Ting and Henrickson disclose a process in which the flavedo was finely chopped and the oil therein dissolved in an aqueous acetone solution.

In *Food Technology, volume* 23, (7), pages 87–90 (1969), Ting and Hendrickson describe their earlier work and disclose the use of an admixture of acetone and hexane as a solvent used to dissolve the oils in the flavedo. The resulting solution was then distilled to remove hexane, limonene and other low boiling point constituents. The authors further describe a technique for purifying the extracted carotenoids chromatographically in conjunction with a Florasil Column.

In the *Journal of Food Science,* volume 35, pages 436–439 (1970), Kew and Berry teach the use of hexane alone as a solvent to dissolve the oils in chopped flavedo, followed by a treatment of the resulting solution with potassium hydroxide; the solution was then washed with water and evaporated. The coloring agents were then steam distilled from the remaining constituents.

In the *Journal of Food Science,* volume 36, pages 1033–1035 (1971), Wilson, Bissett and Berry also made disclosure to a counter-current extraction to further purify the carotenoids derived from peel frits, whole peel and flavedo. The authors described the flavedo input as providing the best yield of color.

A slightly different approach to the problem of carotenoid purification after extraction is taught by Berry, Wilson and Bissett in the *Journal of Food Science,* volume 37, pages 809–811 (1972). In this article, the authors disclosed the use of isopropyl alcohol, following the steam distillation step. Because the carotenoids are soluble in the alcohol and the undesirable constituents are not, these other ingredients were removed by filtering. The carotenoids were then precipitated from the alcohol.

At volume 36 of the *Journal of Food Science,* pages 367–369 (1971), the authors describe a study to determine the stability of the carotenoids during extended periods of storage.

Judah, Burdick, and Carroll, in *Industrial and Engineering Chemistry,* Volume 46 (no. 11), pages 2262–2271 (November 1954). disclose the use of alcohols in a manner similar to that described by Berry, Wilson and Bissett *(Journal of Food Science,* volume 37) as a means for extracting chlorophyl from dried leaf meal.

While the above described techniques provide relatively efficient methods for extracting concentrated amounts of the citrus carotenoids, the resulting product includes amounts of the foreign solvents therein and therefore prevent the use of carotenoids obtained by these methods as additives to certain food products.

There have also been suggestions for using compounds naturally occuring in citrus peel as a solvent for removing the carotenoids from the flavedo. However, these compounds proved unsatisfactory, requiring the use of acetone or similar solvents as a polishing step for final removal of the carotenoids.

In U.S. Pat. No. 3,915,960, which is assigned to the assignee of the present invention, Waite and Jefferson disclose a method for the accelerated winterization of citrus oils.

SUMMARY OF THE INVENTION

The present invention contemplates a method for deriving carotenoids from citrus fruits, and the product resulting therefrom, the method comprising the steps of extracting the oil from the flavedo of the fruit and thereafter removing the unwanted waxes from the oil.

Following the de-waxing step, limonene is removed in a separate step carried out at a moderate vacuum, preferably in a wiped-film evaporator. Thereafter, the output from the limonene removal step is distilled under a low vacuum, on the order of between 10 microns to 1 millimeter of mercury, and at a temperature of between 90° to 120° C. in a molecular still to effect final removal of the balance of the undesirable constituents.

Preferably, the molecular distillation step described above is carried out in two separate steps in which the first step is carried out at a moderate vacuum of between 0.5 to 1 millimeters of mercury, at 90° to 120° C. in order to effect removal of the balance of the limonene, and other constituents such as decanal and linalool. Thereafter, the output of the first molecular distillation step is distilled again in the same, or another molecular still, at a pressure of between about 10–50 microns of mercury and at a temperature of between 100° to 120° C. to remove such constituents as valencene, alpha-sinensal, beta-sinensal and nootkatone. The resulting output is high concentration of the carotenoid agents from the peel oil, in a substantially purified form free of waxes, limonene and other undesirable constituents, and containing no foreign substances, such as the organic solvents described above.

An important aspect of the present invention is the recognition that the desirable carotenoids may be removed from the oil of the flavedo in a series of separate, independent steps wherein portions of the undesirable constituents can be removed by selective treatment, but without the addition of the undesirable foreign substances.

THE DRAWING

The single FIGURE of the drawing is a flow chart illustrating one embodiment of the method in accordance with the present invention.

DESCRIPTION OF THE PREFERRED EMBODIMENT

The carotenoid composition of various citrus fruits has been reported in the literature. By way of example, the carotenoid composition of the pulp and peel of Valencia oranges, navel oranges, tangerines and ruby red grapefruit are set forth in tables I–IV respectively, attached as an appendix hereto. This information is reported by Curl and Bailey in various literature references, including *Agricultural and Food Chemistry*, volume 4, page 156 (1956); *Food Research*, volume 26, page 422 (1961); *Agricultural and Food Chemistry*, volume 5, page 605 (1957); and *Food Research*, volume 22 page 63 (1957).

As a first step in the method of the present invention, whole oranges 11 are first washed and then passed into an extractor 10. For example, a Brown Extractor manufactured by Automatic Machinery Corp. of Winter Haven, Fla. was used in this embodiment. Another suitable extractor is manufactured by Food Machinery Corp. of Princeton, N.J. During the extracting operation, referred to generally as 10 in the drawing, the flavedo of the fruit is treated in a well known manner to destroy the cells containing the peel oil. Water 12 is sprayed over the fruit to form an emulsion 14 with the peel oil, while the juices 16 and the peel byproduct 18 are carried away from the extractor 10.

Thereafter, the oil emulsion 14 is centrifuged at 20 to separate the water 22 and the peel oil 24 therein. At this point, it will be understood by those skilled in the art that there are various techniques for removing peel oil from processed citrus fruits other than the specific example which has been described above.

Following removal of the oil 24 from the emulsion 14, the oil is then passed through a winterizing process to remove the complex combination of wax-like substances, such as the sterols, stearenes, coumarins and other wax-like substances which occur naturally in citrus peel oil, and other types of undesirable, wax-like substances which are applied in packing houses to prevent shrinkage and achieve a pleasing appearance. This winterization 26 may be accomplished in accordance with the aforementioned U.S. Pat. No. 3,915,960 to Waite and Jefferson, the teachings of which are incorporated here by reference. The undesirable waxes 28 are removed as a byproduct of this winterization step 26.

Thereafter, the de-waxed oil is treated in an evaporation and folding step to a concentration of at least 15 fold, and preferably about 20–30 fold, to remove most of the limonene contained in the oil. In this preferred embodiment, the evaporation and folding step is successively carried out in a wiped-film evaporator, such as that manufactured by Luwa Corporation of Charlotte, N.C. This evaporation step was carried out at a temperature of between 65°–75° C. at a pressure of between 15–20 millimeters of mercury. Wiped-film evaporators of the type manufactured by Luwa are conventional apparatus employing an external condensor. The resulting output has a substantial portion of the limonene 32 removed therefrom, on the order of about 95% of the limonene contained in the output of the winterization step 26.

The deterpenated oil (that is, with the limonene 32 removed) is then passed through a molecular distillation process to remove certain undesirable ingredients. In accordance with this preferred embodiment the molecular distillation, referred to generally as 34 in the drawing, is carried out in a two step process. In the first step 36, the output of the evaporation and folding step 30 is distilled at a moderate pressure of between 0.5–1.0 millimeters of mercury and at a temperature of between 90 to 120° C. to remove the balance of the limonene contained in the oil, and such constituents as decanal and linalool. Thereafter, the output of the first molecular distillation step is passed through a second step 40 in a molecular still at a pressure of between 10–50 microns of mercury and at a temperature of between 100° to 120° C. During this process, certain other undesirable constituents such as valencene, alpha-sinensal, beta-sinensal and nootkatone are removed from the oil (note element 42 in the drawing). The resulting output of this molecular distillation process is a concentrated amount of the carotenoids in a substantially pure form, without the addition of the organic solvents described above with respect to the prior art.

In the above description, the term "molecular distillation" is a term of art used to describe commercially available stills of the type in which the condensor is located internally so as to provide a short distance between the evaporator and the condensor. Suitable molecular stills for use in conjunction with this method are manufactured by All Star Equipment Supply Scientific Company of Wolcott, N.Y. and by C.V.C. of Rochester, N.Y. In the above described embodiment, a 12 inch molecular still manufactured by All Star Equipment was used. It has been found that the temperature at which both the molecular distillation steps 36 and 40 are carried out is not critical, so long as the temperature is within the range specified. The lower range of 90° C. or 100° C. is a lower temperature beyond which efficient distillation does not occur. The upper temperature of 120° C. is a temperature at which the oil in the still begins to decompose.

As a modification to the process described above and illustrated in the drawing, it has been found that the output of the evaporation and folding step 30 may be passed through a single molecular distillation step in order to achieve substantial removal of the balance of the limonene and the other ingredients described above, so long as the temperature ranges specified are followed, and so long as the distillation takes place under vacuum within the lower pressure range in the second step 40 and the higher pressure range specified in step 36; that is, between 10 microns to 100 millimeter of mercury. However, the resulting carotenoid output does not appear to be as pure as is obtained from the preferred embodiment described above.

TABLE I

APPENDIX

Carotenoid composition of Valencia orange pulp and peel

| CONSTITUENT | ORANGE PULP, % | FRESH ORANGE PEEL, % |
|---|---|---|
| Phytoene | 4.0 | 3.1 |

TABLE I-continued
APPENDIX
Carotenoid composition of Valencia orange pulp and peel

| CONSTITUENT | ORANGE PULP, % | FRESH ORANGE PEEL, % |
|---|---|---|
| Phytofluene | 13 | 6.1 |
| α-Carotene | 0.5 | 0.1 |
| β-Carotene | 1.1 | 0.3 |
| ρ-Carotene | 5.4 | 3.5 |
| OH-α-Carotenelike | 1.5 | 0.3 |
| Cryptoxanthin epoxidelike | — | 0.4 |
| Cryptoxanthin | 5.3 | 1.2 |
| Cryptoflavinlike | 0.5 | 1.2 |
| Cryptochromelike Lutein | 2.9 | 1.2 |
| Zeaxanthin | 4.5 | 0.8 |
| Capsanthinlike | — | 0.3 |
| Antheraxanthin | 5.8 | 6.3 |
| Mutatoxanthins | 6.2 | 1.7 |
| Violaxanthin | 7.4 | 44 |
| Luteoxanthins | 17 | 16 |
| Auroxanthin | 12 | 2.3 |
| Valenciaxanthin | 2.8 | 2.2 |
| Sinensiaxanthin | 2.0 | 3.5 |
| Trollixanthinlike | 2.9 | 0.5 |
| Valenciachrome | 1.0 | 0.7 |
| Sinensiachromelike | — | 0.2 |
| Trollichromelike | 3.0 | 0.8 |

TABLE II
Carotenoid composition of Naval orange pulp and peel.

| CONSTITUENT | Approx % of Carotenoid Mixture | |
|---|---|---|
| | PULP | PEEL |
| phytoene | 4.3 | 12.1 |
| phytofluene | 4.4 | 7.3 |
| alpha-carotene | 0.12 | 0.03 |
| beta-carotene | 0.5 | 0.15 |
| zeta carotene | 8.5 | 8.4 |
| hydroxy-alpha-carotene | 0.5 | 0.15 |
| cryptoxanthin | 10.0 | 3.1 |
| cryptoxanthin 5,6,5',6'-diepoxide | 0.2 | 0.5 |
| hydroxy-alpha-carotene 5,6 - epoxide | — | 0.10 |
| cryptoxanthin 5,6-epoxide | 0.4 | 0.7 |
| hydroxy-alpha-carotene 5,8-epoxide | — | 0.09 |
| cryptoxanthin 5,6,5',8'-diepoxide | — | 0.04 |
| -cryptoflavin | 0.4 | 4.7 |
| lutein | 1.3 | 0.6 |
| zeaxanthin | 1.5 | 0.8 |
| reticulataxanthin | — | 0.26 |
| antheraxanthin | 11.6 | 3.1 |
| flavoxanthin-like | — | 0.16 |
| mutatoxanthins | 0.5 | 0.6 |
| violaxanthin | 45.6 | 26.4 |
| luteoxanthins | 2.5 | 21.5 |
| auroxanthins | — | 0.3 |
| valenciaxanthin | 2.2 | 1.3 |
| sinensiaxanthin | 2.2 | 2.7 |
| trans-neoxanthin | 0.5 | — |
| valenciachrome | 0.3 | 0.9 |
| trolliflor-like | 0.4 | — |
| trollixanthin-like | 1.2 | 0.8 |
| sinensiaxanthin-like | 0.3 | 1.8 |
| trollichrome-like | 0.17 | — |

TABLE III
Carotenoid composition of Tangerine pulp and peel

| CONSTITUENT | APPROXIMATE % OF TOTAL CAROTENOIDS | |
|---|---|---|
| | PULP | PEEL |
| Phytoene | 5.8 | 4.2 |
| Phytofluene | 7.2 | 3.5 |
| α-Carotene | 0.3 | 0.2 |
| Phytofluenelike | 0.1 | 0.1 |
| β-Carotene | 4.1 | 0.4 |
| ζ-Carotene | 6.9 | 2.0 |
| γ-Carotenelike | 0.1 | — |
| Lycopene | 0.1 | 0.02 |
| Hydroxy- -carotenelike | 1.0 | 0.6 |
| Cryptoxanthin epoxide | 0.9 | 1.4 |
| Cryptoxanthin | 33 | 24 |
| Hydroxy- -carotene furanoxidelike | — | 0.4 |
| Cryptoflavinlike | 0.8 | 3.4 |
| Rubixanthinlike | — | 0.2 |
| Cryptochromelike | — | 0.1 |
| Lutein | 2.9 | 3.3 |
| Zeaxanthin | 3.3 | 3.5 |
| Hydroxy-canthaxanthinlike | 0.1 | 2.7 |
| Antheraxanthin | 9.7 | 6.2 |
| Mutatoxanthins | 2.2 | 2.8 |
| Violaxanthin | 14 | 24 |
| Luteoxanthins | 3.5 | 9.1 |
| Auroxanthins | 0.4 | 1.9 |
| Valenciaxanthin | 0.2 | 0.4 |
| Sinensiaxanthin | 0.2 | 1.1 |
| Trollixanthinlike | 1.0 | 2.6 |
| Trollein | 0.9 | — |
| Trollichromelike | 0.3 | 0.7 |

TABLE IV
Carotenoid composition of Ruby Red grapefruit peel and pulp

| CONSTITUENT | Approximate Percentage in Total Carotenoids | |
|---|---|---|
| | PULP | PEEL |
| Phytoene | 16 | 47 |
| Phytofluene | 4.4 | 14 |
| α- Carotene | — | 0.1 |
| β- Carotene | 27 | 7.2 |
| Phytofluene-like | — | 0.4 |
| Zeta-Carotene | 3.5 | 7.2 |
| Carotene-like | 0.8 | 0.4 |
| Lycopene | 40 | 11 |
| Substance 377 | 0.2 | — |
| Substance 335 | 0.6 | 0.5 |
| "Hydroxy-a-Carotene" | 0.2 | 0.1 |
| Cryptoxanthin | 0.7 | 1.4 |
| Cryptoxanthin-like | 0.4 | — |
| Cryptoflavin-like | — | 1.3 |
| Rubixanthin-like | 0.5 | 0.3 |
| Cryptochrome-like | — | 0.2 |
| Lutein | 0.3 | 0.9 |
| Antheraxanthin | 0.7 | — |
| Violaxanthin (+Zeaxanthin?) | 0.9 | 1.0 |
| Luteoxanthins | 0.4 | 1.8 |
| Mutatoxanthins | 0.4 | 0.2 |
| Valenciachromes | 0.2 | 0.3 |
| Trollichrome-like | — | 0.2 |
| Auroxanthins | 0.3 | 1.6 |

We claim:

1. A solvent-free method for deriving carotenoids from citrus fruit, comprising the steps of:
   mechanically extracting oil from the flavedo of the fruit;
   winterizing said oil to remove the sterols and other unwanted waxes from said oil;
   removing limonene from said dewaxed oil by evaporation; and thereafter
   distilling said oil under vacuum to accomplish separation of said carotenoids from the remaining constituents.

2. The method recited in claim 1 wherein said oil extracting step comprises the steps of:
   mechanically rupturing the flavedo of said citrus fruit; and simultaneously
   spraying water on said flavedo to form an emulsion with said oil.

3. The method recited in claim 2 wherein said oil extracting step comprises the step of centrifuging said emulsion to remove said oil therefrom.

4. The method recited in claim 1 wherein said winterizing step comprises reducing the temperature of said oil for a period of time sufficient to cause said waxes to agglomerate and crystallize.

5. The method recited in claim 1 wherein said limonene removing step comprises the step of evaporating said dewaxed oil until the carotenoid concentration therein is at least about 15-fold.

6. The method recited in claim 5 further comprising the carrying out of said evaporation step at a temperature of between 65°–75° C. and under a vacuum of between 15–20 millimeters, Hg.

7. The method recited in claim 6 further comprising the steps of carrying out said vacuum distilling step at a pressure of between about 10 microns to 1 millimeters, Hg.

8. The method recited in claim 7 further comprising the step of carrying out said vacuum distilling step at a temperature of between 90°–120° C.

9. A solvent-free method for deriving carotenoids from natural orange peel oil, comprising the steps of:
   winterizing said oil to remove sterols, coumarins and other unwanted waxes in said oil;
   evaporating said winterized oil to remove limonene therefrom until the carotenoid concentration therein is at least about 15-fold; and thereafter
   vacuum distilling said oil under temperature and pressure effective to remove the concentrated carotenoids from the remaining constituents.

10. The method recited in claim 9 wherein said evaporation step is carried out in a vacuum.

11. The method recited in claim 10 wherein said evaporating step comprises the steps of successively evaporating said dewaxed oil to about 20-fold.

12. The method recited in claim 11 wherein said distilling step is carried out under vacuum at a pressure of between 10 microns to 1 millimeters, Hg.

13. A method for deriving carotenoids from oranges, comprising the steps of:
   extracting oil from the flavedo of said oranges;
   winterizing said oil to remove the waxes therein;
   deterpenating said dewaxed oil by successively folding said oil to a concentration of at least about 15-fold; and
   vacuum distilling said dewaxed and deterpenated oil at a temperature between about 90°–120° C. at a pressure of between about 10 microns to 1 millimeters, Hg., to remove said carotenoids.

14. A solvent-free method for extracting carotenoids from oranges, comprising the steps of:
   separating the flavedo of said oranges from the remainder thereof;
   mechanically extracting oil from the flavedo of said fruit;
   reducing the temperature of said oil effective to agglomerate the unwanted waxes therein;
   removing said agglomerated waxes from said oil;
   successively evaporating said dewaxed oil in a vacuum at a pressure between about 15 to 20 millimeters, Hg., and at a temperature between 65° to 75° C. to remove the limonene therein and to concentrate the carotenoids therein at least about 15-fold; and
   distilling said wax-and limonene-free oil under vacuum at a pressure of between about 10 microns to 1 millimeters, Hg., to separate said carotenoids from the remaining constituents.

15. The method recited in claim 14 wherein said extracting step comprises the steps of:
   mechanically rupturing the flavedo of said citrus fruit; and simultaneously
   spraying water on said flavedo to form an emulsion with said oil.

16. The method recited in claim 15 further comprising the step of centrifuging said emulsion to separate said oil and said water.

17. A solvent-free method for extracting carotenoids from citrus fruit, comprising the steps of:
   mechanically extracting oil from the flavedo of said fruit;
   winterizing said oil to remove the unwanted waxes from said oil;
   successively evaporating said de-waxed oil under vacuum at a pressure of between 15 to 20 millimeters, Hg., and at a temperature of between 65° to 75° C. to remove most of the limonene therein and fold said oil to a concentration of at least about 20-fold.
   distilling said wax-free and limonene-free oil in a molecular still at a temperature of between about 100° to 120° C. under vacuum at a pressure between 10–50 microns, Hg., to remove such constituents as valencene, alpha-sinensal, beta-sinensal and nootkatone from said carotenoids.

18. The method recited in claim 17 wherein said oil extracting step comprising the steps of:
   mechanically rupturing the flavedo of said citrus fruit; and simultaneously
   spraying water on said flavedo to form an emulsion with said oil.

19. The method recited in claim 18 further comprising the step of centrifuging said emulsion to remove said oil therefrom.

* * * * *